US012721864B2

(12) United States Patent
Rassaf

(10) Patent No.: US 12,721,864 B2
(45) Date of Patent: Sep. 1, 2026

(54) SKIN TREATMENT USING NO

(71) Applicant: Yes2NO GMBH, Dusseldorf (DE)

(72) Inventor: Tienush Rassaf, Essen (DE)

(73) Assignee: Yes2NO GMBH, Dusseldorf (DE)

( * ) Notice: Subject to any disclaimer, the term of this patent is extended or adjusted under 35 U.S.C. 154(b) by 5 days.

(21) Appl. No.: 19/252,324

(22) Filed: Jun. 27, 2025

(65) Prior Publication Data

US 2025/0332193 A1 Oct. 30, 2025

Related U.S. Application Data

(63) Continuation of application No. PCT/EP2023/087988, filed on Dec. 29, 2023.

(60) Provisional application No. 63/486,733, filed on Feb. 24, 2023, provisional application No. 63/477,595, filed on Dec. 29, 2022.

(51) Int. Cl.

| | |
|---|---|
| ***A61K 33/00*** | (2006.01) |
| ***A61K 8/19*** | (2006.01) |
| ***A61K 8/365*** | (2006.01) |
| ***A61K 31/19*** | (2006.01) |
| ***A61P 17/10*** | (2006.01) |
| ***A61P 17/14*** | (2006.01) |
| ***A61Q 7/00*** | (2006.01) |
| ***A61Q 19/08*** | (2006.01) |

(52) U.S. Cl.

CPC ................ *A61K 33/00* (2013.01); *A61K 8/19* (2013.01); *A61K 8/365* (2013.01); *A61K 31/19* (2013.01); *A61P 17/10* (2018.01); *A61P 17/14* (2018.01); *A61Q 7/00* (2013.01); *A61Q 19/08* (2013.01); *A61K 2800/72* (2013.01)

(58) Field of Classification Search

CPC .......... A61K 33/00; A61K 8/19; A61K 8/365; A61K 31/19; A61P 17/10; A61P 17/14; A61Q 7/00; A61Q 19/08

See application file for complete search history.

(56) References Cited

U.S. PATENT DOCUMENTS

| | | | | |
|---|---|---|---|---|
| 2003/0175362 | A1 | 9/2003 | Kross et al. | |
| 2012/0096906 | A1 | 4/2012 | Mahaney et al. | |
| 2016/0206632 | A1 | 7/2016 | Kross | |
| 2021/0093539 | A1* | 4/2021 | LaRosa .................. | A61K 8/416 |

FOREIGN PATENT DOCUMENTS

| | | | | | |
|---|---|---|---|---|---|
| EP | 3158990 | B1 | | 6/2018 | |
| WO | 2020227367 | A1 | | 11/2020 | |
| WO | WO 2020/227367 | | * | 11/2020 | ............. A61K 38/44 |

OTHER PUBLICATIONS

Mintel; (Jan. 15, 2021 95% natural soothing lotion Data base No. 8413641).*

International Application Serial No. PCT/EP2023/087988, International Search Report and Written Opinion mailed Apr. 26, 2024; 16 pages.

* cited by examiner

*Primary Examiner* — Shirley V Gembeh

(74) *Attorney, Agent, or Firm* — Garrett H. Anderson

(57) ABSTRACT

Compositions, methods and systems relating to the delivery of NO to intradermal targets are disclosed. Such delivery allows perturbation of molecular signaling such as may impact skin health, acne, aging, or hair follicle health. The compositions methods and systems overcome obstacles that inhibit effective delivery of NO in concentrations sufficient to influence intradermal signaling.

30 Claims, 5 Drawing Sheets

Fig. 1

$NO_2$
$NO_2$
$NO_2$
$NO_2$
$H^+$
$H^+$
$H^+$
$H^+$
$H^+$
Transport molecule
NO
NO
NO
NO
Epidermis
Dermis
Subcutaneous tissue

SKIN TREATMENT USING NO

CROSS-REFERENCE TO RELATED APPLICATIONS

This document is a Continuation of PCT/EP2023/087988, filed Dec. 29, 2023, which claims benefit of priority to U.S. Provisional Application Ser. No. 63/477,595, filed Dec. 29, 2022, and to U.S. Provisional Application Ser. No. 63/486,733, filed Feb. 24, 2023, to each of which is hereby incorporated by reference in its entirety.

BACKGROUND

Nitric oxide (NO) is an important mediator in several mechanisms which are important for maintaining skin homeostasis. NO is crucial for maintaining and regaining skin health, by or example inhibiting inflammation, inhibiting differentiation of inflammatory cell types, and promoting circulation and circulatory development.

However, delivery of NO to the regions of the skin where it is most efficacious is problematic. NO has a very short half live, which is dependent on dose and on its environment. The half-life ranges from milliseconds in aqueous solution down to microseconds when in contact with oxygenated hemoglobin in circulating blood. Equally challenging is the fact that NO does not readily traverse the epidermal membrane barrier, so that very little topically applied NO is able to access the intradermal space where it is most effective in modulating skin health.

SUMMARY

Disclosed herein are compositions, methods and systems relating to the delivery of NO to a skin site on a user, so as to allow the NO to access intradermal regions of the skin site. NO is stably retained in a precursor composition prior to administration to the skin site. NO is released as active NO upon application at the skin site. Upon release, the NO is transiently bound by NO binding moieties in NO-binding moiety complexes that facilitate delivery and release of NO to intradermal regions of the skin.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 1 presents an NO delivery schematic diagram.

DETAILED DESCRIPTION

Figure 2:
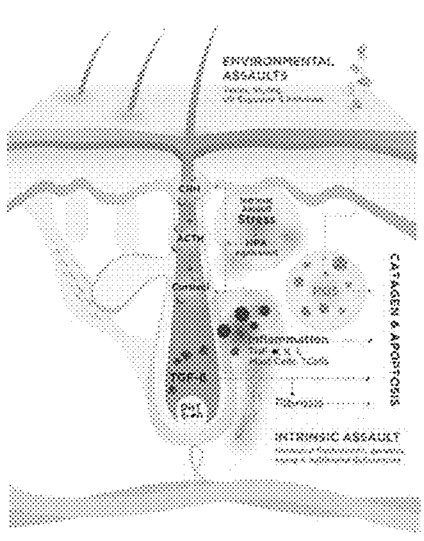
FIG. 2 presents internal and external factors influencing hair loss.

Disclosed herein are compositions, systems and methods related to the delivery of nitric oxide (NO) to intradermal targets toward the goal of improving skin health. Through practice of the disclosure herein, skin health is improved as measured by decreases in pimples, acne, reducing wrinkles or other signs of skin damage or aging, or improvements in hair growth.

Delivery of NO to intradermal targets is problematic, as NO does not readily pass through the epidermis, and readily diffuses out of most delivery media such that even contacting NO to the skin in effective concentrations is difficult.

Through the present disclosure, these obstacles are overcome through a number of biochemical approaches, leading to effective treatment of skin disorders such as pimples, acne, skin damage from aging, or baldness such as male and female pattern baldness.

Figure 1:
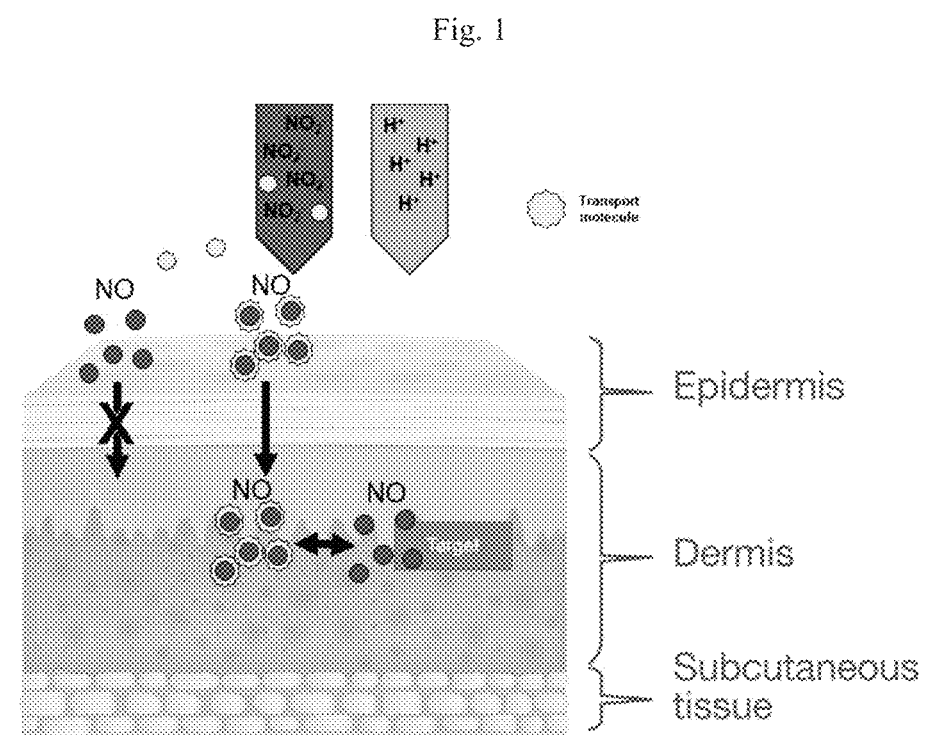

Firstly, delivery of NO in the form of stable precursors, such as Sodium nitrite, which are degraded to release NO only immediately prior to or concurrent with administration to the skin of a subject. NO is formulated in a carrier under conditions in which it is bound as a stable precursor, such as Sodium nitrite. Concurrent with or immediately or shortly prior to administration to the skin of a subject, carrier conditions are changed such that an NO precursor is destabilized and NO is released into the carrier. See FIG. 1.

Alternately or in combination, carriers are formulated to comprise a NO binding moiety that forms a transient complex with free NO so as to retain released NO in the carrier, and to facilitate transport of the NO, via the complex, across barriers such as epidermal barriers, so as to deliver NO to subdermal or intradermal spaces within a subject. See FIG. 1.

Thus using the approaches above, alone or in tandem, one is able to retain NO precursor molecules in a precursor formulation, release the NO upon bringing the composition into contact with a target region such as patient skin, and then bind the free NO into a transient complex to facilitate retention of active NO and delivery of active NO across epidermal barriers into subdermal or intradermal spaces, where the NO may act to improve skin health, such as by improving acne, revitalizing skin or triggering improved hair growth. See FIG. 1.

NO delivered intradermally serves to inhibit inflammation responses, inhibit or kill microbes contributing to acne, increase blood flow, or otherwise increase local skin health. By overcoming the obstacles to NO delivery, the technology of the present disclosure accesses the potential for NO to improve skin health, particularly but not limited to reducing acne, counteracting the negative effects of aging on skin, and improving hair growth, each of which are discussed in more detail herein.

Compositions

Consistent with the delivery of NO to subdermal and intradermal locations, disclosed herein are compositions for the retention of NO precursors, the release of those precursors, capture of released NO by transient complexes, so as to facilitate delivery of NO across epidermal membranes and release of NO intradermally, where it is under some theories believed to be particularly efficacious in improving skin health, such as reducing acne, reducing the effects of aging, or improving hair growth. The compositions described herein are consistent with use in the methods and systems described elsewhere herein. Similarly, the composition herein are in some cases compositions for use in practicing the methods described herein.

Some such compositions are formulated to retain NO precursor molecules under carrier conditions that prevent loss of NO prior to delivery to a target site, such as facial or scalp tissue, or other skin surface.

NO precursor molecules are molecules that comprise a nitrogen and an oxygen atom in a stable configuration under a first chemical environment, and which release at least one NO molecule under a second chemical environment. Exemplary precursor molecules include nitrites ($NO_2^-$), often nitrite salts such as Sodium nitrite, Calcium nitrite, Ammonium nitrite, or Potassium nitrite. Alternate precursor molecules include nitrate salts, such as Sodium nitrate, and other molecules comprising at least one nitrogen atom and at least one oxygen atom stably bound under one set of conditions but subject to degradation under a second set of conditions to yield at least one free NO molecule.

Precursor molecules stably retain NO under a first set of conditions and release it under a second set of conditions, such that release of NO can be modulated by modulating the releasing condition or conditions. Using the nitrite salts as examples, under basic conditions of pH 8 or greater, or otherwise in the absence of a releasing acid, nitrite is stable in aqueous solution. Stability of the composition as a whole is often increased by addition of one or more of ascorbic acid, erythorbic acid, or alpha-tocopherol, which serves to prevent nitrosamine and higher order N-oxide formation. Upon reduction of the pH to 7.5 or lower, or otherwise upon contacting to a releasing acid such as an AHA, nitrite degrades to form molecular nitrogen gas $N_2$ and NO. Thus by changing the pH of the local environment of an NO precursor, one may modulate NO release into a carrier composition.

Accordingly, some NO precursor compositions comprise one or more population of NO precursor molecule, such as a nitrite salt, for example Sodium nitrite, Calcium nitrite, Ammonium nitrite, or Potassium nitrite, or any other molecules comprising at least one nitrogen atom and at least one oxygen atom stably bound under one set of conditions but subject to degradation under a second set of conditions to yield at least one free NO molecule. Such a molecule may be present in a broad range of concentrations consistent with the disclosure herein, such as less than, about or at least 0.01%, 0.02%, 0.05%, 0.1%, 0.2%, 0.3%, 0.4%, 0.5%, 0.6%, 0.1%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, or more than 20%.

NO precursor compositions are often aqueous, and may comprise one or more additional components in addition to the one or more NO precursor molecule species. Some additional components serve to stabilize the NO precursor species, such as to prevent NO precursor reactions such as nitrosamine formation. Exemplary stabilizers include, for example, ascorbic acid, erythorbic acid, or alpha-tocopherol, among others.

NO precursor compositions are routinely buffered, so as to maintain a first condition or environment under which the NO precursor is stable. Buffers may maintain a first condition, such as a first pH, for example a pH of at least 7, at least 7.5, at least 8, at least 8.5, at least 9, at least 10 or greater. Generally, releasing acids such as AHA (glycolic acid, citric acid, lactic acid, among others listed herein) are not included in the precursor composition, as they may impact NO precursor stability NO precursor compositions may additionally comprise an NO binding moiety, such as a molecule that may bind released NO so as to retain it in a composition and to facilitate the transport of NO across a barrier such as an epidermal membrane. In particular, non-AHA NO binding moieties, such as NO binding proteins, are in some cases included in the NO precursor composition. An NO binding moiety molecule may be present in a broad range of concentrations consistent with the disclosure herein, such as less than, about or at least 0.01%, 0.02%, 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, or more than 20%. In some cases, NO binding moieties also serve as buffers. Generally, NO binding moieties that additionally impact NO precursor stability are excluded from the precursor composition, so as to maintain NO-precursor stability.

NO precursor compositions are in some cases selected for compatibility to a target tissue such as facial skin, aged or damaged skin, or scalp. Some precursor compositions comprise antibiotics, anti-inflammatory components, fragrances, salves or other components to independently facilitate a therapeutic outcome. Some compositions are not animal tested or do not comprise animal products. Some compositions are vegan.

Various precursor compositions comprise one or more of the following components: hyaluronic acid, ascorbic acid, retinyl palmitate, tocopherol acetate, Sodium hydroxide, Sodium nitrite, polyacrylate, Salicylic acid, succinoglycan, glycerin, ascorbyl glucoside, Sodium citrate, carbomer, sodium chloride, sodium sulfate, geraniol, linalool, benzyl benzoate, citronellol, hexyl cinnamal, phenoxyethanol, ethylhexyl glycerin, allantoin, or other stabilizers, buffers, fragrances, or texture-impacting components. Any one of such a molecule may be present in a broad range of concentrations consistent with the disclosure herein, such as less than, about or at least 0.01%, 0.02%, 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, or more than 20%.

Some precursor compositions beneficially comprise an antibiotic or antimicrobial component. Antimicrobials consistent with the disclosure herein comprise beta-lactams, macrolides, quinolones, tetracyclines or aminoglycosides, essential oils such as oils of bay, cinnamon, clove and thyme, or other plant derived antimicrobials such as salicylic acid. Some exemplary precursor compositions comprise essential oils such as oils of bay, cinnamon, clove and thyme. Some exemplary precursor compositions comprise a plant derived antimicrobial such as salicylic acid. Any one of such a molecule may be present in a broad range of concentrations consistent with the disclosure herein, such as less than, about or at least 0.01%, 0.02%, 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 179, 18%, 19%, 20%, or more than 20%.

NO precursor compositions deliver NO precursors to a site or preserve NO precursors so that NO is available at a target site. However, to release the NO, a precursor composition must be contacted to or activated by a releasing composition, such as a composition that changes a precursor composition at a first condition or set of conditions to an active composition at a second composition or set of conditions.

Releasing compositions differ from precursor compositions in at least one parameter, such that mixing of a precursor composition and a releasing composition results in a change from a first condition or set of conditions in which an NO precursor molecule is stable to a second condition or set of conditions in which an NO precursor molecule degrades to yield NO. Often, a releasing composition differs from a precursor composition in its pH, such that upon mixing the releasing composition and the precursor composition results in a change in the resulting active composition pH so as to facilitate or effect NO release from its precursor molecule.

Exemplary releasing compositions may have a pH less than that of a precursor composition, such as a pH of no more than 1, 2, 3, 4, 5, 6, or 7. Various ratios of precursor compositions and releasing compositions may be mixed to from an active composition. In various cases, a releasing composition constitutes at least, about or at most 10%, 20%, 30%, 40%, 50%, 60%, 70%, 80%, or 90% of the resulting active composition, such as 30%-70%, 40%-60%, or about or exactly 50%. Often, the relative proportion of precursor and releasing compositions is related to the relative difference in the parameter resulting in the difference from the first condition to the second condition, such that for example a releasing composition differing very dramatically from a precursor composition may be added in a relatively low proportion and nonetheless effect a change from a first condition in the precursor composition to a second condition in the resulting activating composition sufficient to release NO.

Releasing compositions are often aqueous, and may comprise one or more constituents in common with a precursor composition. For example, a releasing composition may comprise one or more of the following components: hyaluronic acid, retinyl palmitate, tocopherol acetate. Sodium hydroxide, polyacrylate, Salicylic acid, succinoglycan, glycerin, ascorbyl glucoside. Sodium citrate, carbomer, sodium chloride, sodium sulfate, geraniol, linalool, benzyl benzoate, citronellol, hexyl cinnamal, phenoxyethanol, ethylhexyl glycerin, allantoin, or other stabilizers, buffers, fragrances, or texture-impacting components. Such a molecule may be present in a broad range of concentrations consistent with the disclosure herein, such as less than, about or at least 0.01%, 0.02%, 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, or more than 20%.

Some releasing compositions beneficially comprise an antibiotic or antimicrobial component. Antimicrobials consistent with the disclosure herein comprise beta-lactams, macrolides, quinolones, tetracyclines or aminoglycosides, essential oils such as oils of bay, cinnamon, clove and thyme, or other plant derived antimicrobials such as salicylic acid. Some exemplary precursor compositions comprise essential oils such as oils of bay, cinnamon, clove and thyme. Some exemplary releasing compositions comprise a plant derived antimicrobial such as salicylic acid. Any one of such a molecule may be present in a broad range of concentrations consistent with the disclosure herein, such as less than, about or at least 0.01%, 0.02%, 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, or more than 20%.

Releasing compositions are in some cases selected for compatibility to a target tissue such as facial skin or scalp. Some precursor compositions comprise antibiotics, anti-inflammatory components, fragrances, salves or other components to independently facilitate a therapeutic outcome. Some compositions are not animal tested or do not comprise animal products. Some compositions are vegan. Some releasing compositions, however, exhibit a pH or other parameter outside of a range suitable for administration to skin of an individual in the absence of mixing with a precursor composition.

Releasing compositions may additionally comprise an NO binding moiety, such as a molecule that may bind released NO so as to retain it in a composition and to facilitate the transport of NO across a barrier such as an epidermal membrane. Exemplary molecules include alpha hydroxy acid (AHA) molecules, such as glycolic acid, lactic acid, citric acid, hydroxycaprilic acid and hydroxycapric acid. Such a molecule may be present in a broad range of concentrations consistent with the disclosure herein, such as less than, about or at least 0.01%, 0.02%, 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, or more than 20%. Alternately, non-AHA NO binding moieties are also consistent with the disclosure herein, such as NO binding proteins. In some cases NO binding moieties also serve as buffers.

Active compositions arise from mixing a precursor composition and a releasing composition. Active compositions are characterized by having a 'second condition' state that facilitates release of NO from a precursor molecule.

Active compositions comprise and result from mixtures of precursor compositions and releasing compositions. Accordingly, active compositions are often relatable to precursor and releasing compositions according to the concentrations at which these compositions are mixed to from active compositions.

Active compositions are often aqueous, and may comprise one or more additional components in addition to the one or more NO precursor molecule species. Some additional components serve to stabilize the NO precursor species, such as to prevent NO precursor reactions such as nitrosamine formation. Exemplary stabilizers include, for example, ascorbic acid, erythorbic acid, or alpha-tocopherol, among others.

Active compositions are routinely buffered, so as to maintain a second condition or environment under which the NO precursor is unstable and NO is released. Buffers may maintain a second condition, such as a first pH, for example a pH of no more than, about or at least 5, 6, 7, 7.5, or greater than 7.5.

Active compositions may additionally comprise an NO binding moiety, such as a molecule that may bind released NO so as to retain it in a composition and to facilitate the transport of NO across a barrier such as an epidermal membrane. Exemplary molecules include alpha hydroxy acid (AHA) molecules, such as glycolic acid, lactic acid, citric acid, hydroxycaprilic acid and hydroxycapric acid. Such a molecule may be present in a broad range of concentrations consistent with the disclosure herein, such as less than, about or at least 0.01%, 0.02%, 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, or more than 20%. Alternately, non-AHA NO binding moieties are also consistent with the disclosure herein, such as NO binding proteins. In some cases NO binding moieties also serve as buffers.

Active compositions differ from precursor compositions in part because of the presence of NO molecules, such as NO molecules released from precursor molecules in the precursor composition. In some cases these NO molecules are unbound or 'free' in solution. Alternately, in some cases at least some of these NO molecules are bound by NO binding moieties such as AHA molecules to from NO binding moiety complexes. These complexes do not comprise covalent bonds between the NO molecules and the NO binding moieties such as AHA molecules. However, these complexes do transiently form, and the presence of these complexes further distinguishes active compositions from precursor compositions or releasing compositions.

Accordingly, in some cases activating compositions comprise NO binding complexes comprising NO bound to alpha hydroxy acid (AHA) molecules, such as glycolic acid, lactic acid, citric acid, hydroxycaprilic acid and hydroxycapric acid, to form noncovalent complexes of NO-glycolic acid, NO-lactic acid, NO-citric acid, NO-hydroxycaprilic acid and NO-hydroxycapric acid, respectively. These noncovalent NO binding moiety complexes are much less stable than, for example, NO precursor compounds. Nonetheless, these NO binding moiety complexes retain NO in the active compositions for a much longer time than free NO would otherwise be retained in solution.

Furthermore, NO binding moiety complexes exhibit biochemical properties that differ from those of free NO molecules, such that NO binding moiety complexes are, for example, more readily able to diffuse across a hydrophobic barrier such as an epidermal skin barrier. Free NO is reactive and readily, rapidly diffuses into the air surrounding the activated composition. This complicates the ability to deliver an efficacious amount of NO to a target region or tissue, particularly an intradermal region. Consequently, NO binding moiety complexes are able to access subdermal or intradermal regions of the skin that may not be readily accessed by free NO molecules.

Without being bound by theory, it is proposed that these features of NO binding moiety complexes facilitate intradermal or subcutaneous delivery of NO. Free NO is transiently bound, so as to retain it in active compositions. Transiently bound NO is more readily able to traverse epidermal membranes so as to access the intradermal or subcutaneous portions of the skin or regions below the skin. As the NO binding moiety complexes are transient, the NO will at some biologically relevant frequency be released from NO binding moiety complexes subsequent to localization to the intradermal or subcutaneous portions of the skin or regions below the skin. Accordingly, active compositions facilitate the delivery of NO across epidermal membranes, so that NO may impact intradermal or subcutaneous cell signaling pathways, such as cell differentiation, inflammation, circulatory development, or other pathways relevant to skin health.

Active compositions are in some cases selected for compatibility to a target tissue such as facial skin or scalp. Some precursor compositions comprise antibiotics, anti-inflammatory components, fragrances, salves or other components to independently facilitate a therapeutic outcome. Some compositions are not animal tested or do not comprise animal products. Some compositions are vegan.

Various active compositions comprise one or more of the following components: hyaluronic acid, ascorbic acid, retinyl palmitate, tocopherol acetate, Sodium hydroxide, polyacrylate, Salicylic acid, succinoglycan, glycerin, ascorbyl glucoside, Sodium citrate, carbomer, sodium chloride, sodium sulfate, geraniol, linalool, benzyl benzoate, citronellol, hexyl cinnamal, phenoxyethanol, ethylhexyl glycerin, allantoin, or other stabilizers, buffers, fragrances, or texture-impacting components. Such a molecule may be present in a broad range of concentrations consistent with the disclosure herein, such as less than, about or at least 0.01%, 0.02%, 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, or more than 20%. In some cases an active composition comprises one or more of an antibiotic, an antimicrobial, an exfoliant, or a skin softener.

Some active compositions beneficially comprise an antibiotic or antimicrobial component. Antimicrobials consistent with the disclosure herein comprise beta-lactams, macrolides, quinolones, tetracyclines or aminoglycosides, essential oils such as oils of bay, cinnamon, clove and thyme, or other plant derived antimicrobials such as salicylic acid. Some exemplary precursor compositions comprise essential oils such as oils of bay, cinnamon, clove and thyme. Some exemplary active compositions comprise a plant derived antimicrobial such as salicylic acid. Any one of such a molecule may be present in a broad range of concentrations consistent with the disclosure herein, such as less than, about or at least 0.01%, 0.02%, 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, or more than 20%.

Active compositions are in some cases selected for compatibility to a target tissue such as facial skin or scalp. Some precursor compositions comprise antibiotics, anti-inflammatory components, fragrances, salves or other components to independently facilitate a therapeutic outcome. Some compositions are not animal tested or do not comprise animal products. Some compositions are vegan.

An active composition is formed from a mixture of at least one precursor composition and at least one releasing composition. A number of mixing approaches are consistent with the disclosure herein. In some cases the at least one precursor composition and at least one releasing composition are formulated as salves or other relatively viscous formulations so that they may be applied directly to the skin and mixed 'by hand' by a user, for example by co-applying them and mixing them together while rubbing them into the skin at a target area.

Alternately, in some cases the at least one precursor composition and at least one releasing composition are formulated as substantially aqueous liquids. As above, they may be applied directly to the skin and mixed 'by hand' by a user, for example by co-applying them and mixing them together while rubbing them into the skin at a target area. Alternately, at least one precursor composition and at least one releasing composition may be mixed immediately or shortly prior to applying to the skin, for example by co-extruding each into a common chamber and subjecting them to mixing via mechanical agitation, shaking, co-swirling, co-extruding onto a target region of a user, or other approach. In yet another approach, the at least one precursor composition and at least one releasing composition are applied as an aerosol, for example onto the scalp of a user, using a spray drawn from the common chamber or comprising parts drawn from a precursor composition chamber and a release composition chamber in proportions sufficient to activate release of the NO concurrent with generation or projection of the aerosol or liquid flow, or upon contact of the aerosol or liquid flow to a target region such as the scalp of a user.

Various compositions benefit from mixing prior to or concurrently with application to a target site. Mixing is variously effected by at least 1 second, 5 seconds, 15 seconds, 30 seconds, 60 seconds, 5 minutes or more. Alternately, to avoid loss of released NO, mixing is in some cases effect in no more than 1 second, 5 seconds, 15 seconds, 30 seconds, 60 seconds, or 2 minutes.

Methods

Consistent with the delivery of NO to subdermal and intradermal locations, disclosed herein are methods for the release of NO precursors, capture of released NO by transient complexes, and delivery of NO across epidermal membranes and release of NO intradermally, where it is under some theories believed to be particularly efficacious in improving skin health, such as reducing acne, reducing the effects of aging, or improving hair growth. The methods described herein are consistent with use of the compositions and systems described elsewhere herein.

Methods disclosed herein result in the mixing of NO precursor compounds in precursor compositions with releasing compositions so as to result in conditions at the NO precursor compounds conducive to or resulting in NO release.

Through the methods herein, NO precursor compounds such as Sodium nitrite salts are stably maintained indefinitely under stable first conditions, such as a pH about or at least 8. Upon addition of a releasing composition, the resulting activating composition is brought to a second condition, such as a pH of no greater than, for example about 7.5, so as to destabilize the NO precursor compound and release free molecular NO.

A number of first conditions and second conditions are consistent with the disclosure herein.

As mentioned above, some precursor compounds such as nitrite are stabilized at first pH of at least 8, such as 8, 8.5, 9, 9.5, 10, 10.5 or greater than 10.5. Upon mixing with a releasing composition, the resultant activated composition exhibits a second pH below that of the stabilizing pH, such that molecular NO is released. The second pH is in various cases no greater than, for example, 9, 8.5, 8, 7.5, 7, 6.5, 6, 5, 4, or less than 4. This change in stabilization conditions arises from the releasing composition exhibiting a pH substantially lower than the activated composition pH, such that the mixing of the precursor composition and the releasing composition comes to a releasing condition pH. A number of releasing composition parameters and mixing parameters may come to this result. In some cases, the releasing composition exhibits a condition that is substantially lower than that of the precursor condition, such that only a small proportion of the activation composition is represented by releasing composition, but nonetheless the activation composition is pushed to the second, or activating condition parameter such as reduced pH. Alternately, in some exemplary embodiments, precursor and releasing compositions are combined in ratios of about or effectively 50%/50% or 1:1 ratios. This approach allows achievement of the activating second condition in the activation composition, at a relatively minimal difference between precursor and releasing compositions at the releasing parameter. This reduces the need for dramatic differences between precursor and releasing compositions, so as to minimize the risk of harm at the point of application which may arise from incomplete mixing of compositions.

Although pH is provided as a first exemplary embodiment, alternative approaches to NO release are contemplated herein and understood in the art. NO may be bound in a thermosensitive composition, such that heating prior to administration results in generation of an activation composition. Heating may be sufficient on its own, or in combination with addition of the releasing composition.

In some cases the precursor composition and the releasing composition may comprise reagents which when in contact undergo an exothermic reaction, thereby providing heat to release NO from NO precursor compounds. Similarly, in some cases shaking or other mechanical disruption may be sufficient to release NO from NO precursor molecules. This shaking may be sufficient on its ow, in which case release compositions are not required, or may be effective only upon addition or mixing of precursor and release compositions.

Mixing. Mixing of the precursor composition is effected through a number of approaches consistent with the disclosure herein. Mixing is in some cases effected in situ, such that precursor and releasing compositions are concurrently applied to skin of a subject, such as skin exhibiting acne, exhibiting age-related degradation, or exhibiting reduced hair growth. Mixing may then be accomplished by hand, concurrently with massaging the resulting activation composition into a target skin region.

Alternately, mixing is in some cases effected prior to application to the target skin surface. For example, precursor and releasing compositions are concurrently introduced into a dedicated chamber of a composition carrying device, and mix either without additional effort or through shaking, inversion or other kinetic or mechanical interruption. Activation composition may then be extruded from the dedicated chamber, either as a paste or salve for delivery onto the skin, or released as an aerosol or other spray.

Various compositions benefit from mixing prior to or concurrently with application to a target site. Mixing is variously effected by at least 1 second, 5 seconds, 15 seconds, 30 seconds, 60 seconds, 5 minutes or more. Alternately, to avoid loss of released NO, mixing is in some cases effect in no more than 1 second, 5 seconds, 15 seconds, 30 seconds, 60 seconds, or 2 minutes. Mixing is effected variously on the target surface, in the hands or on the fingers of a user, or in a chamber such as a mixing chamber into which the precursor composition and releasing composition are co-delivered prior to application to a target surface.

Various mixing proportions are consistent with the disclosure herein. Precursor composition and releasing composition are mixed in various proportions, such as 10%-90%, 20%-80%, 30%-70%, 40%-60%, 50%-50%, 60%-40%, 70%-30%, 80%-20%, or 90%-10%, or any proportion spanned by the range of proportions listed herein, such as 35%-65%. Mixing proportions are selected by various criteria. In some cases proportions are selected so as to effect a change from a first condition state in a precursor composition to a second condition state in the activation composition. Proportions may be selected so as to effect such a change from a first condition state in a precursor composition to a second condition state in the activation composition such that the releasing composition does not need to have condition that, prior to mixing, may be harmful to a delivery region such as skin.

Retention and Delivery of free NO. Consistent with the disclosure herein, NO is delivered to intradermal or subdermal regions of the skin. This NO is in some cases NO released from NO precursor molecules, although de novo applied NO is also suitably delivered.

Free NO is not readily delivered to effective target sited because it both readily diffuses out of compositions applied to skin and into the surrounding air, and because it does not effectively pass the barrier of the epidermis.

Through the methods herein, free NO is retained in activation compositions at the site of administration, and is effectively delivered across epidermal membranes so as to access intradermal or subdermal molecular signaling targets.

NO retention and delivery is effected by the formation of NO binding moiety complexes of NO and NO binding moieties. An NO binding moiety is a molecule that may bind released NO so as to retain it in a composition and to facilitate the transport of NO across a barrier such as an epidermal membrane. Exemplary molecules include alpha hydroxy acid (AHA) molecules, such as glycolic acid, lactic acid, citric acid, hydroxycaprilic acid and hydroxycapric acid. Such a molecule may be present in a broad range of concentrations consistent with the disclosure herein, such as less than, about or at least 0.01%, 0.02%, 0.05%, 1%, 2%, 3%, 4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, or more than 20%. Alternately, non-AHA NO binding moieties are also consistent with the disclosure herein, such as NO binding proteins. In some cases NO binding moieties also serve as buffers.

NO binding moiety complex formation and dissolution occur at comparable rates in some working compositions. That is, particularly compared to NO precursor compositions, NO binding moiety compositions are unstable, and the binding complex population is a dynamic balance between complex formation and NO release.

The timescale of NO release is often longer than that of complex transport across the epidermis, such that some NO which is transported across the epidermis or into an intradermal or subepidermal space is then released. NO which is released into the intradermal or subepidermal space is them available to act on molecular or cellular signaling which occurs in either of these spaces. This results in a significant increase in efficacy of NO treatment over topical administration of unbound NO.

Delivery of NO into the intradermal or subcutaneous space of the skin allows targeting or modulation of a number of molecular signaling pathways relevant to skin health, acne modulation or hair growth.

A number of signaling moieties impact acne formation or resolution. These are believed to include, among others, IGF1, the signaling complex mTORC1, SREBP1, PPAR ligands, Androgen and associated regulatory neuropeptides, dietary lipids, and bacterial antigens. This signaling moieties may in turn impact epithelial proliferation, hyperseborrhoea, or inflammation. Inflammation and epithelial proliferation, in turn, influence or are influenced by NLRP3 caspase complexes, which signal through pro-IL-1beta to form IL-1beta, alone or in combination with IL-1R to activate TO differentiation into Th17 cells, as well as IL-17 and specific NO-Treg Foxp3 negative cells. Accordingly, some methods herein comprise targeting one or more of the signaling moieties above, or other signaling moieties or pathways known in the art to be impacted by NO, even if in the art, delivery of NO to the relevant locations necessary to target these signaling moieties is problematic. Some such methods comprise practicing the steps herein or administering the compositions herein, and may further comprise measuring an output of such a signaling moiety, such as phosphorylation of a substrate or observation of an outcome of such signaling, for example differentiation of a cell type or activation of a cellular or tissue level response, for example wound healing, hair growth or hair retention, acne reduction, or reduction in wrinkle density.

Delivery of NO into intradermal tissues allows one to target these signaling moieties, so as to impact inflammation responses relevant to acne. In particular. NO intradermal delivery may result in a number of molecular changes relevant to acne reduction. These include any of the following. Intradermal NO may lead to decreased production of IL-1beta, which is associated with inhibition of both capsase-1 and NLRP3 inflammasome activation, which decreases IL-1beta expression and provides downstream inhibition of pro-inflammatory cytokine release. Intradermal NO may lead to decreased IL-17 production, associated with inhibition of TH17 helper cell proliferation and function, and induction of T-regulatory (Foxp3 negative) cells that inhibit Th17 cell activation. Intradermal NO may lead to decreased E-selectin expression on endothelial cells, associated with the suppression of lymphocyte diapedesis resulting in decreased trafficking of inflammatory cells to the perifollicular region, decreased expression of vascular adhesion molecules and decreased perifollicular inflammation. Intradermal NO may also lead to regulation of matrix metalloproteinase activity and inti-inflammatory cytokines, which may affect dermal matrix tissue restoration through modulation of MMPs and cytokines associated with would healing and tissue repair.

Accordingly, the disclosure herein allows and relates to modulation of any one or more of these signaling pathways, molecules or targets for the amelioration of acne. In some cases one or more signaling pathways, molecules or targets are selected to be targeted. Similarly, in some cases one or more of these pathways, molecules or targets are selected to be targeted, and then targeted through administration of NO such as through delivery of NO intradermally as disclosed herein, and then an outcome related to molecular signaling involving the targeted pathway, molecule or target is monitored, alone or in combination with monitoring of acne status for the individual to which the NO is administered.

Acne amelioration may be measured through a number of approaches consistent with the disclosure herein. For example acne may be measured by the global acne grading system (GAGS), through the dermatology life quality index (DLQI), alone or in combination with any number of measurements relating to acne density, conspicuousness, discomfort, persistence or other measure. GAGS efficacy measurements may be in some cases a percent change of at least 10% at two weeks, at least 30% at four weeks, or at least 40% at 8 weeks. Similarly, DLQI measurements may be a percent change of at least 30% in two weeks, at least 60% at four weeks, or at least 60% at six weeks. Improvements at two weeks are in various embodiments at least 10%, 20%, 30%, 40%, 50%, 60%, 70%, 80%, 90%, 100%. Similarly, improvements at four weeks are in various embodiments at least 10%, 20%, 30%, 40%, 50%, 60%, 70%, 80%, 90%, 100%. Similarly, improvements at six weeks are in various embodiments at least 10%, 20%, 30%, 40%, 50%, 60%, 70%, 80%, 90%, 100%. Similarly, improvements at eight weeks are in various embodiments at least 10%, 20%, 30%, 40%, 50%, 60%, 70%, 80%, 90%, 100%. Similarly, measurements may be made at 1, 2, 3, 4, 5, 6, 7, 8, 9 10, 15, 20 or more than 20 weeks, and percent changes may be observed of at least 5%, 10%, 15%, 20%, 25%, 30%, 35%, 40%, 50%, 75% or more.

Much like acne, baldness such as male pattern baldness is mediated by signaling that occurs in the dermis or below the epidermis. A number of signaling moieties impact male pattern balding. These are believed to include, among others, CRH, ACTH, Cortisol, TNF-alpha, IL-1, TGF-beta, DHT, 5-alphaR, and Reactive Oxygen Species, among others. Similarly, the dermis is believed to be a site of action of external and internal insults that impact the onset of male pattern balding, such as toxins, UV exposure, pollution, stress, hormonal fluctuations, nutritional deficiencies, aging, and genetic factors.

Amelioration of balding such as male pattern balding may be measured through a number of approaches consistent with the disclosure herein. For example, amelioration may be measured by cumulative hair thickness, by number of follicular units per unit area, or by any of a number of other measurements of hair thickness, hair density, hair length or hair resistance to abcission.

Cumulative hair thickness measurements may be in some cases a percent change of at least 10% at twelve weeks, or at least 25% at 24 weeks. Measurements of the number of follicular hair units per unit area may be a percent change of at least 5% at twelve weeks, or at least 14% at 24 weeks.

Improvements at twelve weeks are in various embodiments at least 10%, 20%, 30%, 40%, 50%, 60%, 70%, 80%, 90%, 100%. Similarly, improvements at eighteen weeks are in various embodiments at least 10%, 20%, 30%, 40%, 50%, 60%, 70%, 80%, 90%, or in some cases up to 100%. Similarly, improvements at twenty four weeks are in various embodiments at least 10%, 20%, 30%, 40%, 50%, 60%, 70%, 80%, 90%, or in some cases up to 100%. Similarly, measurements may be made at 1, 2, 3, 4, 5, 6, 7, 8, 9 10, 15, 20 or more than 20 weeks, and percent changes may be observed of at least 5%, 10%, 15%, 20%, 25%, 30%, 35%, 40%, 50%, 75% or more.

Delivery of NO into intradermal tissues allows one to target these signaling moieties, so as to impact inflammation responses relevant to hair growth related to countering the effects of male pattern baldness. In particular, NO intradermal delivery may result in a number of molecular changes relevant to countering the effects of male pattern baldness. These include any of the following: increased blood flow, inhibition of steroidogenesis, reduction of inflammation, promotion of hair follicle formation or hair growth, an increase in the number of hair follicles, development of hair follicle stem cell development, an increase hair regeneration, an increase hair shaft elongation, a decrease in androgens, a decrease in sebocyte proliferation, or a decrease in lipid synthesis.

Accordingly, the disclosure herein allows and relates to modulation of any one or more of these signaling pathways, molecules or targets for the amelioration of baldness, such as male pattern baldness. In some cases one or more signaling pathways, molecules, targets, or receptors of an internal or external stressor are selected to be targeted. Similarly, in some cases one or more of these pathways, molecules, targets, or receptors of an internal or external stressor are selected to be targeted, and then targeted through administration of NO such as through delivery of NO intradermally as disclosed herein, and then an outcome related to molecular signaling involving the targeted pathway, molecule or target is monitored, alone or in combination with monitoring of acne status for the individual to which the NO is administered.

Amelioration of balding such as male pattern balding may be measured through a number of approaches consistent with the disclosure herein. For example, amelioration may be measured by cumulative hair thickness, by number of follicular units per unit area, or by any of a number of other measurements of hair thickness, hair density, hair length or hair resistance to abscission.

Cumulative hair thickness measurements may be in some cases a percent change of at least 10% at twelve weeks, or at least 25% at 24 weeks. Increases number of follicular hair units by more than 5% after 12 weeks and at least 14%, and in some cases more than 20% within 24 weeks. Similarly, measurements may be made at 1, 2, 3, 4, 5, 6, 7, 8, 9 10, 15, 20 or more than 20 weeks, and percent changes may be observed of at least 5%, 10%, 15%, 20%, 25%, 30%, 35%, 40%, 50%, 75% or more.

Improvements at twelve weeks are in various embodiments at least 10%, 20%, 30%, 40%, 50%, 60%, 70%, 80%, 90%, 100%. Similarly, improvements at eighteen weeks are in various embodiments at least 10%, 20%, 30%, 40%, 50%, 60%, 70%, 80%, 90%, 100%. Similarly, improvements at twenty four weeks are in various embodiments at least 10%, 20%, 30%, 40%, 50%, 60%, 70%, 80%, 90%, 100%.

Much like acne and baldness, skin aging is mediated by signaling that occurs in the dermis or below the epidermis. A number of signaling moieties impact skin aging or skin health. These are believed to include, among others, Cortisol, TNF-alpha, IL-1, TGF-beta, DHT, 5-alphaR, UV radiation, and Reactive Oxygen Species, among others. Similarly, the dermis is believed to be a site of action of external and internal insults that impact skin aging related health, such as toxins, UV exposure, pollution, stress, hormonal fluctuations, nutritional deficiencies, aging, and genetic factors.

Delivery of NO into intradermal tissues allows one to target these signaling moieties, so as to impact inflammation responses relevant to countering the effects of skin aging. In particular, NO intradermal delivery may result in a number of molecular changes relevant to countering the effects of skin aging or of aging on skin health. These include any of the following: increased blood flow, inhibition of steroidogenesis, reduction of inflammation, increased stem cell activity, increased epidermal apoptosis, or other responses related to improving skin cell health.

Accordingly, the disclosure herein allows and relates to modulation of any one or more of these signaling pathways, molecules or targets for the amelioration of baldness, such as male pattern baldness. In some cases one or more signaling pathways, molecules, targets, or receptors of an internal or external stressor are selected to be targeted. Similarly, in some cases one or more of these pathways, molecules, targets, or receptors of an internal or external stressor are selected to be targeted, and then targeted through administration of NO such as through delivery of NO intradermally as disclosed herein, and then an outcome related to molecular signaling involving the targeted pathway, molecule or target is monitored, alone or in combination with monitoring of acne status for the individual to which the NO is administered.

A number of treatment regimens are consistent with practice of the methods and application of the compositions herein. Treatment regimens are in some cases selected so as to improve, maximize or increase the time during which NO-activated effects are impacting the target tissues—such as reductions in inflammation related signaling pathways or increases in signaling related to circulation or hair follicle related differentiation or apoptosis inhibition. These effects on signaling may last on the order of hours, so some exemplary treatment regimens are selected to re-activate these signaling effects at about the time when a previous administration's effect on signaling has worn off.

This duration is often not correlated to NO occupancy of intradermal regions. So long as NO is present in the intradermal region in sufficient concentration for sufficient time to impact signaling, the signaling perturbation may long outlast the duration of the NO occupancy. Accordingly, in some cases a treatment regimen is selected to optimize or increase the proportion of time during which the signaling is perturbed. Some treatment regimens are selected to maintain a steady perturbation state for a targeted signaling pathway. Other treatment regimens are selected to provide NO occupancy for a minimum amount of time necessary to effect signaling perturbation. Yet other treatment regimens are selected to allow some 'gap' or recovery time between intervals of signaling perturbation events.

Application is preferably at least daily, such as once, twice, three times or more than three times daily. Some application regimens comprise a single application per day. Some application regimens comprise two applications per day. Some application regimens comprise three applications per day. Application is often at regular intervals, such as every 12 hours, every 8 hours, or before and after sleep, or once daily. Application is in some cases subsequent to washing the region to be treated. Application is often followed by allowing the activation composition to dry on or be absorbed at the site of application. In exemplary embodiments the site of application is not washed until substantially after application, such as at least 5, 10, 15, 20, 30, or 60 minutes after application, preferably at least 20 minutes after application. Alternately, the composition is not removed or the site of application is not washed for at least 1, 2, 3, 4, 6, or 8 hours after application.

A broad range of dosages is consistent with the disclosure herein. Dosage, as measured by volume of medicament applied, is often selected as a function of the area to be treated. Compositions are often administered in aliquots of less than, at least or about 100 uL, 200 uL, 300 uL, 400 uL, 500 uL, 1 mL, 1.5 mL, 2 mL or greater, and aliquots are variously administered singly, two at a time, three at a time, four at a time, five at a time or greater than four at a time, either in total or per unit area of the skin to be targeted. Dosage is selected in some cases to fully cover the target area.

Beneficially, in some cases application does is not accompanied by system side effects such as impact on heart rate, vein diameter or blood pressure. Some application regimens comprise measuring blood pressure, such as may be done as a precaution to assay for changes in blood pressure, such as pursuant to administration of compositions herein. As there is often no impact on blood pressure through application of the compositions or practice of the methods herein, administration regimens are in some cases undertaken for at least 1 month, 2 months, 3 months, 6 months, 1 year, or in some cases indefinitely. Some alternative treatment regimens, in contrast, elicit one or more systemic side effects, such as changes in blood pressure, that may limit duration of application of the compositions.

Methods disclosed herein variously comprise ongoing monitoring, or endpoint monitoring so as to facilitate improvement calculations. Accordingly, some methods comprise performing an initial measurement, followed by practice of one or more of the steps described elsewhere herein. Similarly, some methods comprise receiving an initial diagnosis, followed by practice of one or more of the steps described elsewhere herein. Such a diagnosis may relate generally to a condition to be addressed, such as wound healing, acne reduction, hair growth or wrinkle reduction. Alternately or in combination, such a diagnosis may comprise identification of a particular pathway to be modulated, or a particular pathway endpoint product to be suppressed or triggered, and may further comprise measurement of an impact upon that particular outcome, such as signaling reduction or increase or cell differentiation reduction or increase. Measurements may be made at 1, 2, 3, 4, 5, 6, 7, 8, 9 10, 15, 20 or more than 20 weeks, and percent changes may be observed of at least 5%, 10%, 15%, 20%, 25%, 30%, 35%, 40%, 50%, 75% or more.

Systems

Consistent with the compositions and methods above, disclosed herein are systems for the formulation, mixing and delivery to a subject of medicaments for ameliorating or resolving skin ailments, such as acne, aging related skin damage, or hair loss such as male pattern baldness, or for targeting a signaling pathway such as one implicated in one of these ailments or otherwise active subcutaneously, for example as mentioned elsewhere herein. Systems described herein are contemplated for use of the compositions disclosed herein, and for practice of the methods disclosed herein.

A first set of systems is configured to deliver viscous precursor compositions and releasing compositions to a subject's skin, such as acne skin or skin exhibiting aging damage, or otherwise identified as a treatment target. The precursor and releasing compositions are delivered to a target area either concurrently or in quick succession, where they may be mixed in situ by a user, such as pursuant to rubbing the resultant activation composition into the skin. Mixing is variously effected by at least 1 second, 5 seconds, 15 seconds, 30 seconds, 60 seconds, 5 minutes or more. Alternately, to avoid loss of released NO, mixing is in some cases effect in no more than 1 second, 5 seconds, 15 seconds, 30 seconds, 60 seconds, or 2 minutes.

These systems often comprise a first chamber harboring a precursor composition and a second chamber harboring a releasing composition. Each of these chambers is configured to hold a volume of its respective reagent consistent with the ratio with which the two compositions are mixed to yield the activation composition. That is, in embodiments where the compositions are mixed at a 50%/50% ratio to form the activation composition, the first chamber and the second chamber are of equal or approximately equal volume. Alternately, for example, when the precursor and releasing compositions are to be mixed in, say, a 75%/25% ratio, then the first and second chambers are similarly configured in a 3:1 ratio of volumes.

The first chamber and second chamber are in some cases separate, independent containers, such that they may be manipulated independently of one another. Alternately, the first chamber and second chamber are physically attached so that they may be handled together.

Similarly, a first chamber opening and a second chamber opening are in some cases distinct from one another, such that their respective contents may be separately or distinctly extruded onto a subject target region. Alternately, some systems comprise a first chamber and a second chamber having openings that share a common exit route, such that the precursor composition and the releasing composition are extruded through a common opening or pursuant to a common process such as pressing a single pump. In these embodiments, the exit route is often configured so that there is no communication between the first chamber and the second chamber, so that the compositions are not in contact other than immediately prior to, concurrent with or immediately subsequent to being commonly extruded.

A second set of systems is configured to extrude a thin or watery precursor compositions and releasing compositions to a subject's skin, such a subject's scalp or other target area. The precursor and releasing compositions are delivered to a target area either concurrently or in quick succession, where they may mix in situ. Often, delivery is in the form of an aerosol, liquid spray, or a pump-dispensed liquid bolus flow.

The precursor and releasing compositions are in some cases pre-mixed into an activation composition prior to delivery to a site on the user such as the scalp. Premixing is in some cases concurrent with formation of an aerosol, liquid spray or a dispensed liquid bolus, such that premixing to form the activation composition occurs concurrently with delivery to the site such as the scalp, aged or damaged skin or acne. Mixing is variously effected by at least 1 second, 5 seconds, 15 seconds, 30 seconds, 60 seconds, 5 minutes or more. Alternately, to avoid loss of released NO, mixing is in some cases effect in no more than 1 second, 5 seconds, 15 seconds, 30 seconds, 60 seconds, or 2 minutes.

The precursor and releasing compositions are in some cases mixed into an activation composition concurrent with delivery to a site on the user such as the scalp. Mixing is in some cases concurrent with formation of an aerosol, liquid spray or a dispensed liquid bolus, such that mixing to form the activation composition occurs concurrently with delivery to the site such as the scalp, aged or damaged skin or acne. Mixing may be further effected by the user rubbing the resultant composition at the target area.

Alternately or in combination, premixing is in some cases effected in a dedicated third chamber into which the precursor and releasing compositions are introduced in appropriate proportions to form an activation composition upon mixing. The third chamber brings the precursor and releasing compositions into contact, and is optionally connected to the first chamber and to the second chamber such that compositions introduced into the third chamber do not communicate with or return to the first chamber or the second chamber, thus preserving additional unreacted volumes of the precursor composition and the releasing composition for subsequent use. Alternately, in some cases the third chamber is configured to accommodate all of the contents of the first chamber and the second chamber, such that the contents of a system are exhausted in a single application. Mixing is variously effected by at least 1 second, 5 seconds, 15 seconds, 30 seconds, 60 seconds, 5 minutes or more. Alternately, to avoid loss of released NO, mixing is in some cases effect in no more than 1 second, 5 seconds, 15 seconds, 30 seconds, 60 seconds, or 2 minutes.

Subsequent to or concurrent with mixing in the third chamber, all or a portion of the contents of the third chamber, which may be the activation composition or incompletely mixed precursor and releasing compositions, are extruded as an aerosol, liquid spray or a dispensed liquid bolus for delivery to a target region of a user, such as the scalp, an age-related damaged area, or an acne area, or other target area.

Turning to the Figures, one sees the following.

At FIG. 1, one sees a schematic of the compositions and methods, and effect of use of the systems, as disclosed herein. At top, nitrite (NO2−) and NO-binding moieties ("Transport molecule") are delivered to the surface of the skin via a first precursor composition, at top left chevron arrow. Free protons in the form of a low pH composition are co-delivered to the skin in a releasing composition, top right chevron arrow. Mixing of these compositions results in an activation composition, which releases free NO. Free NO transiently remains in solution but does not efficiently cross into the intradermal region of the skin, indicated by the X-arrow at left. NO-binding moieties are also provided into the activation composition, and exist in both free and NO-bound forms. NO-binding moiety complexes form (at center), and are able to more readily cross the epidermis to access the intradermal region of the skin. These NO-binding moiety complexes are sufficiently stable to carry NO into the intradermal area but do not retain NO indefinitely. Accordingly, some NO carried into the intradermal region is released, where it is able to act on a number of molecular signaling pathways.

At FIG. 2, one sees some signaling pathways and causative agents that negatively impact skin health. External stresses such a toxins, styling. UV exposure and pollution may induce or generate accumulation of reactive oxygen species (ROS) in the dermis or intradermal space. Internal stresses may lead to HPA equivalent induction of CRH, ACTH and Cortisol. Imbalances in TGF-beta and dihydroxytestosterone (DHT) or 5-alpharductase (5-alphaR) acting at the base of hair follicles may also lead to dermal stress. Similarly, TNF-alpha. IL-1, Mast cells and TCells may trigger inflammation in the dermis. All of these stresses, internal and external, lead to catagen and apoptosis in the dermis, resulting in hair loss and reduced skin health. NO, when delivered to the intradermal region of the skin, may modulate the signaling potency of one or more of these stressing agents, so as to alleviate or counteract their negative impact on skin health.

Figure 3:
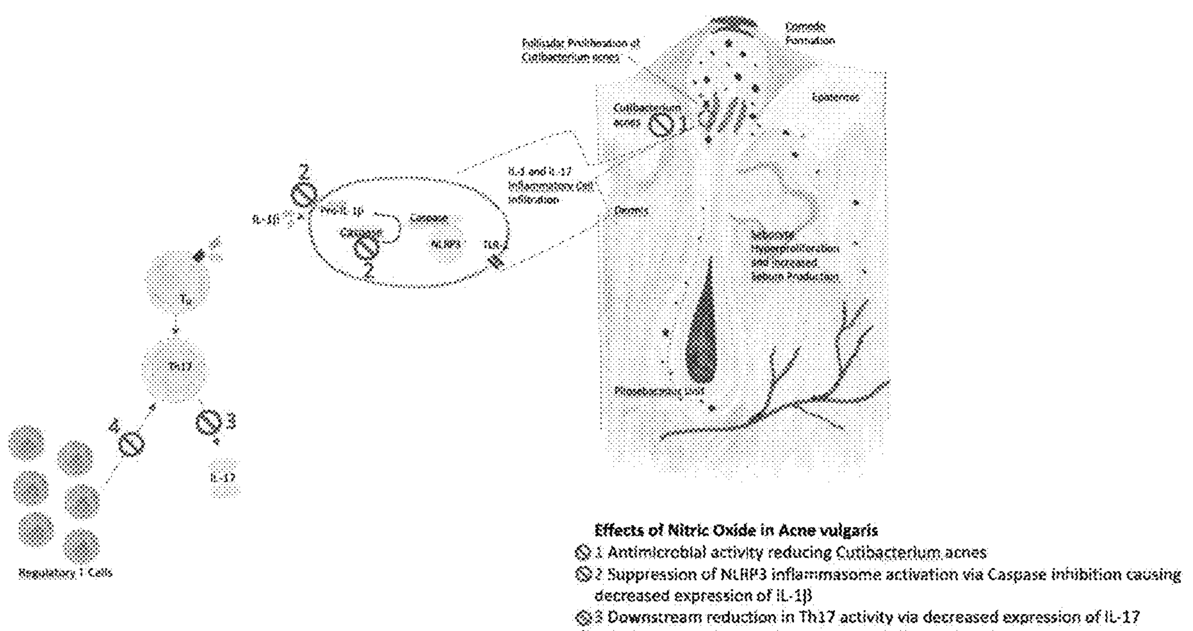
FIG. 3 presents effects of NO in Acne vulgaris.

At FIG. 3 one sees effects of NO on Acne vulgaris. NO antibacterial activity reduces *Cutibacterium acnes*. NO suppresses NLRP3 inflammasome activation via Caspase inhibition causing decreased expression of IL-1beta. NO leads to downstream reduction in Th17 activity via decrease expression of IL-17. Also, NO-stimulated Regulatory T Cells inhibit Th7 activity.

NO is also known to affect signaling pathways and agents that negatively impact (that is, promote) acne formation and skin health acting in the intradermal region. Signaling factors such as IGF1, the signaling complex mTORC1 and SREBP act to modulate Androgen accumulation, PPAR ligands and regulatory neuropeptides, as well as regulating or acting on environmental factors such as lipid accumulation, bacterial antigens and smoking impact, which in turn influence epithelial hyberproliferation, hyperseborrhoea with pro-inflammatory lipids, inflammation and acne related bacterial accumulation. All of these responses may negatively impact skin health. All, also, represent modulation targets that are accessed by efficient NO delivery to the intradermal region. Intradermal NO provides the opportunity to modulate these signaling pathways so as to alleviate their negative impact on acne formation or persistence, on skin health and on hair follicle health, activity or persistence.

Inflammation pathways are known to negatively impact acne formation and skin health acting in the intradermal region. Pro-inflammatory strains of acne-genic bacteria such as *P. acnes* proliferate at follicles at the epidermis/dermis border. These trigger or promote inflammatory responses involving IL-1 and IL-17. Also impacted are signaling pathways involving TLR-2 cellular import pores, NLRP3 Caspase complexes, pro-IL-1beta maturation into IL-1beta, which is exported and sensed by IL-1R receptors which promote TO differentiation into TH17, impacting IL-17 levels and interacting with specific NO-Treg cells (Foxp3 negative). Each of these signaling moieties represents a target accessible by intradermally delivered NO, such as is disclosed herein.

Figure 4:
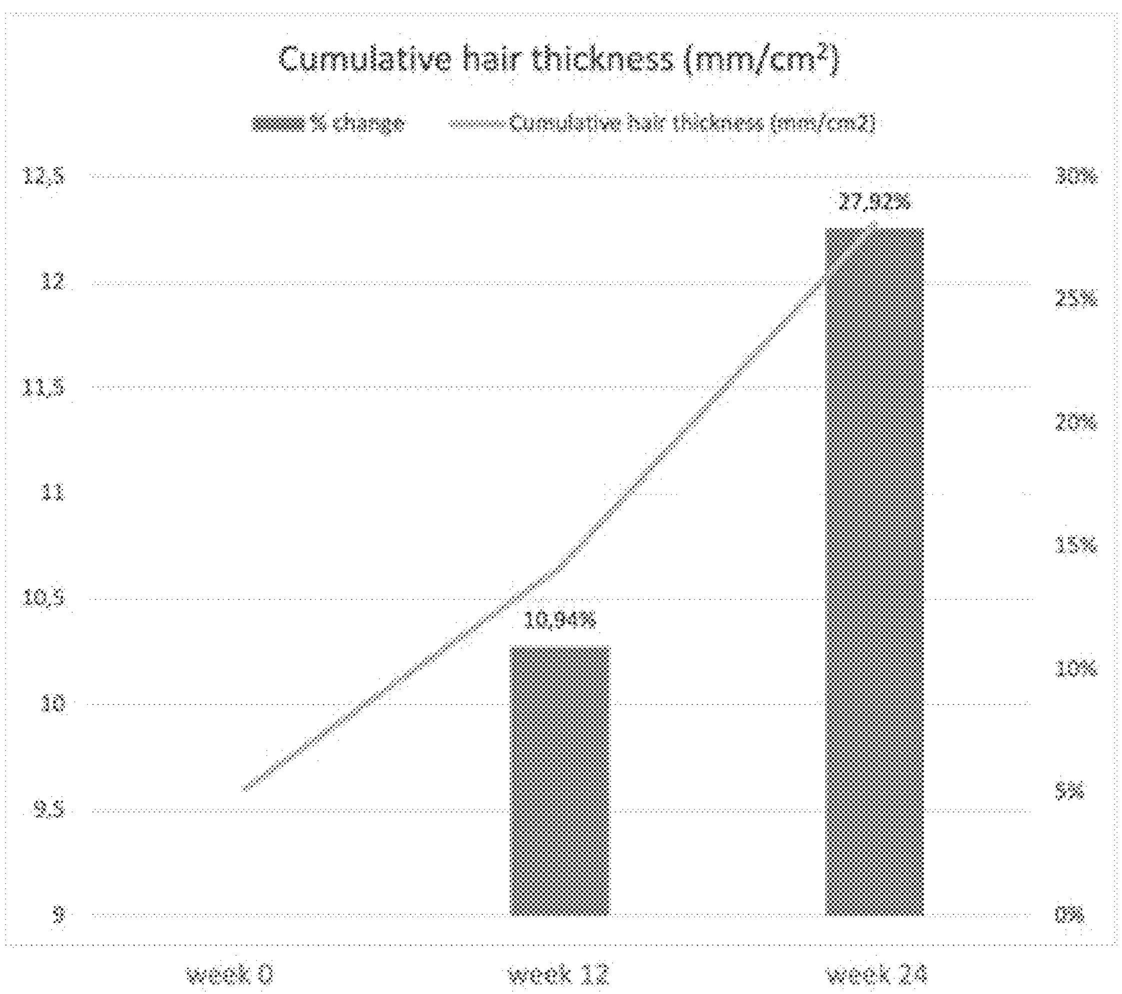
FIG. 4 presents results indicating the effect of a composition herein on cumulative hair thickness over a 24 day treatment regimen.

At FIG. 4, one sees a measurement of the effect of a composition herein on skin health, as measured by cumulative hair length per unit area (mm/cm2), over a 24 week treatment regimen. Data were collected at weeks 0, 12 and 24, and relative improvement at weeks 12 and 24 are presented. The x-axis indicates time in 12 week intervals from week 0 to week 24. The y-axis presents percent change relative to week zero. Results for the trial were averaged. Improvement is 10.94% at week 12, and 27.92% at week 24. One clearly sees that the treatment regimen improved cumulative hair thickness as measured.

Figure 5:
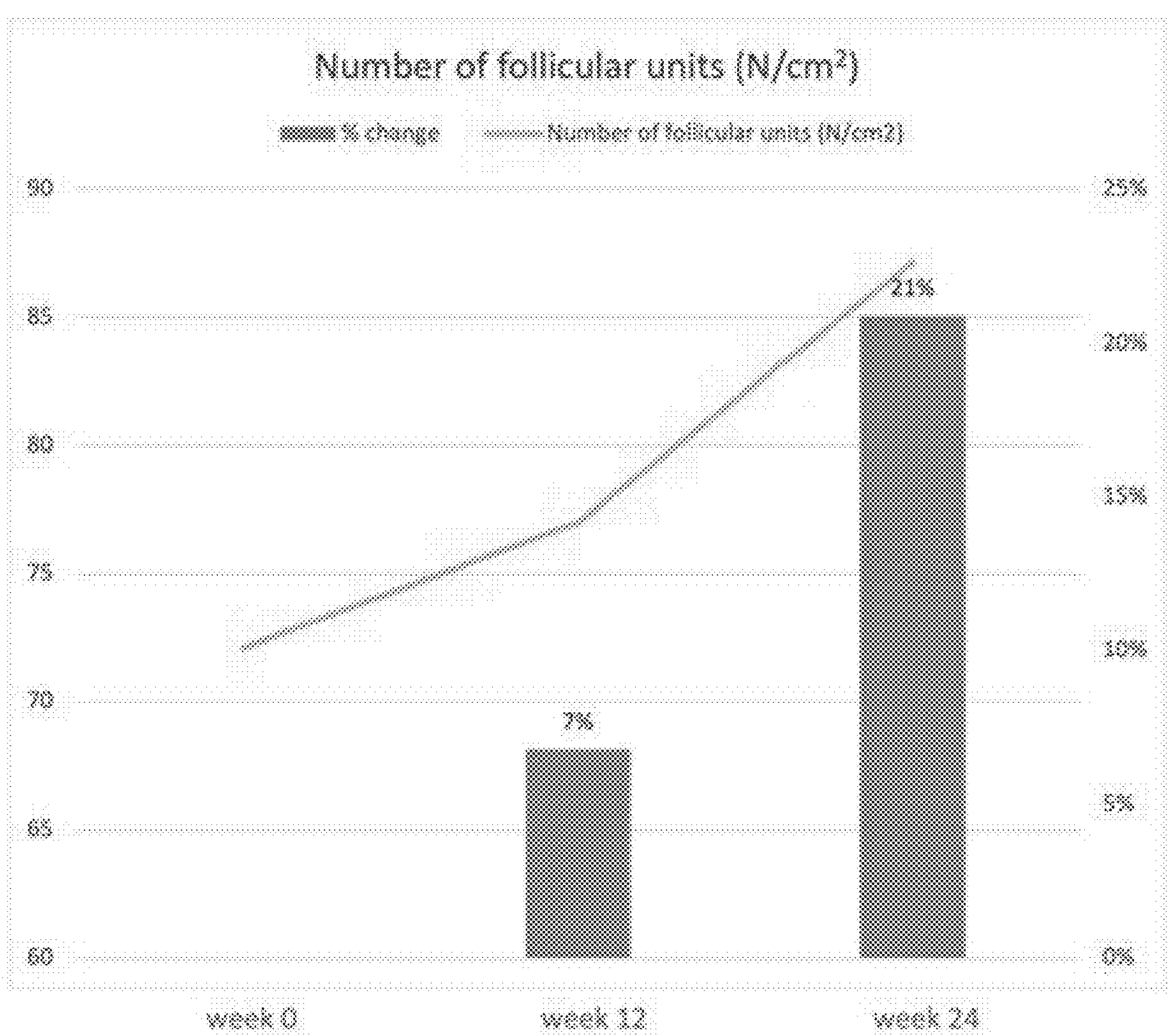
FIG. 5 presents results indicating the effect of a composition herein on hair follicle number over a 24 day treatment regimen.

At FIG. 5, one sees a measurement of the effect of a composition herein on skin health, as measured by number of follicular hair units per unit area (mm/cm2), over a 24 week treatment regimen. Data were collected at weeks 0, 12 and 24, and relative improvement at weeks 12 and 24 are presented. The x-axis indicates time in 12 week intervals from week 0 to week 24. The y-axis presents percent change relative to week zero. Results for the trial were averaged. Improvement is 7% at week 12, and 21% at week 24. One clearly sees that the treatment regimen improved cumulative hair thickness as measured.

The technology is further understood through the following listing of numbered embodiments. 1. A composition comprising an aqueous carrier, an alpha-hydroxy acid (AHA) at a concentration of from 0.1.20%, a nitric oxide (NO) precursor at a concentration of from 0.01-1%, 2. The composition of any previous embodiment, such as embodiment 1, wherein the AHA is glycolic acid. 3. The composition of any previous embodiment, such as embodiment 1 or embodiment 2, wherein the AHA is present at a concentration of 1%-5%, 4. The composition of any previous embodiment, such as embodiments 1-3, wherein the NO precursor is Sodium nitrite. 5. The composition of any previous embodiment, such as embodiments 1-4, wherein the NO precursor is present at a concentration of 0.001-0.5%, 6. The composition of any previous embodiment, such as embodiments 1-5, comprising glycol. 7. The composition of any previous embodiment, such as embodiment 6, wherein the glycol is present at a concentration of 1-20%, 8. The composition of any previous embodiment, such as embodiment 7, wherein the glycol is present at a concentration of 2.5-5%, 9. The composition of any previous embodiment, such as embodiments 1-8, comprising hyaluronic acid. 10. The composition of any previous embodiment, such as embodiments 1-9, comprising retinyl palmitate. 11. The composition of any previous embodiment, such as embodiments 1-10, comprising tocopherol acetate. 12. The composition of any previous embodiment, such as embodiments 1-11, comprising Sodium hydroxide. 13. The composition of any previous embodiment, such as embodiments 1-12, comprising polyacrylate. 14. The composition of any previous embodiment, such as embodiments 1-13, comprising Salicylic acid. 15. The composition of any previous embodiment, such as embodiments 1-14, comprising succinoglycan. 16. The composition of any previous embodiment, such as embodiments 1-15, comprising glycerinascorbic acid. 17. The composition of any previous embodiment, such as embodiments 1-16, comprising ascorbyl glucoside. 18. The composition of any previous embodiment, such as embodiments 1-17, comprising Sodium citrate. 19. The composition of any previous embodiment, such as embodiments 1-18, comprising carbomer. 20. The composition of any previous embodiment, such as embodiments 1-19, comprising sodium chloride. 21. The composition of any previous embodiment, such as embodiments 1-20, comprising sodium sulfate. 22. The composition of any previous embodiment, such as embodiments 1-21, comprising geraniol. 23. The composition of any previous embodiment, such as embodiments 1-22, comprising linalool. 24. The composition of any previous embodiment, such as embodiments 1-23, comprising benzyl benzoate. 25. The composition of any previous embodiment, such as embodiments 1-24, comprising citronellol. 26. The composition of any previous embodiment, such as embodiments 1-25, comprising hexyl cinnamal. 27. The composition of any previous embodiment, such as embodiments 1.26, comprising phenoxyethanol. 28. The composition of any previous embodiment, such as embodiments 1-27, comprising ethylhexylglycerin. 29. The composition of any previous embodiment, such as embodiments 1-28, comprising allantoin. 30. The composition of any previous embodiment, such as embodiments 1 to 29, wherein the composition is vegan. 31. The composition of any previous embodiment, such as embodiments 1 to 29, wherein the composition is hypoallergenic. 32. The composition of any previous embodiment, such as embodiments 1 to 29, for use in ameliorating a skin disorder. 33. The composition of any previous embodiment, such as embodiments 1 to 29, for use in ameliorating acne. 34. The composition of any previous embodiment, such as embodiments 1 to 29, for use in ameliorating wrinkles. 35. The composition of any previous embodiment, such as embodiments 1 to 29, for use in ameliorating hair loss. 36. A method of formulating a composition for use in ameliorating a skin disorder, comprising mixing a first constituent comprising an aqueous carrier and an alpha-hydroxy acid (AHA) at a concentration of from 0.1-20%, and a second constituent comprising an aqueous carrier and a nitric oxide (NO) precursor at a concentration of from 0.01-1%, 37. The method of any previous embodiment, such as embodiment 36, wherein the first constituent and the second constituent are mixed in about equal proportions. 38. The method of any previous embodiment, such as embodiments 36-37, wherein the first constituent and the second constituent are mixed prior to packaging the composition for use in ameliorating a skin disorder. 39. The method of any previous embodiment, such as embodiments 36-38, wherein the first constituent and the second constituent are mixed immediately prior to administering to skin having a skin disorder. 40. The method of any previous embodiment, such as embodiments 36-39, wherein the first constituent and the second constituent are mixed on skin of an individual having a skin disorder. 41. The method of any previous embodiment, such as embodiments 36-40, wherein the first constituent and the second constituent are mixed in an aerosol administered to skin of an individual having a skin disorder. 42. The method of any previous embodiment, such as embodiments 36-41, wherein the first constituent comprises a chemical any previous embodiment, such as embodiments 6 to 29. 43. The method of any previous embodiment, such as embodiments 36-42, wherein the second constituent comprises a chemical any previous embodiment, such as embodiments 2 to 29. 44. The method of any previous embodiment, such as embodiments 36.43, wherein the skin disorder comprises acne. 45. The method of any previous embodiment, such as embodiments 36-44, wherein the skin disorder comprises wrinkles. 46. The method of any previous embodiment, such as embodiments 36-45, wherein the skin disorder comprises hair loss. 47. A method of ameliorating an acne disorder, comprising administering a composition comprising an aqueous carrier, an alpha-hydroxy acid (AHA) at a concentration of from 0.1-20%, a nitric oxide (NO) precursor at a concentration of from 0.01-1%; monitoring acne status, and observing an acne status improvement. 48. The method of any previous embodiment, such as embodiment 47, wherein the administration comprises mixing a first constituent comprising an aqueous carrier and an alpha-hydroxy acid (AHA) at a concentration of from 0.1-20%, and a second constituent comprising an aqueous carrier and a nitric oxide (NO) precursor at a concentration of from 0.01-1%, 49. The method of any previous embodiment, such as embodiments 47-48, wherein the administration comprises topical administration. 50. The method of any previous embodiment, such as embodiment 49, wherein the topical administration results in intradermal delivery of NO to a target. 51. The method of any previous embodiment, such as embodiment 49, wherein the topical administration results in decreased IL. 1 beta production. 52. The method of any previous embodiment, such as embodiment 49, wherein the topical administration results in decreased IL 17 production. 53. The method of any previous embodiment, such as embodiments 49-52, wherein the topical administration results in decreased E selectin expression on endothelial cells. 54. The method of any previous embodiment, such as embodiments 49-53, wherein the topical administration results in modulation of metaloprotienase activity. 55. The method of any previous embodiment, such as embodiments 49-54, wherein the topical administration results in modulation of anti-inflammatory cytokines. 56. The method of any previous embodiment, such as embodiments 49-55, wherein the topical administration results in intradermal antimicrobial activity. 57. The method of any previous embodiment, such as embodiments 49-56, wherein the topical administration results in reduced inflammation. 58. The method of any previous embodiment, such as embodiments 49-57, wherein the topical administration results in reduced lipid biogenesis. 59. The method of any previous embodiment, such as embodiments 49-58, wherein the topical administration results in reduced sebum production. 60. The method of any previous embodiment, such as embodiments 49-59, wherein the topical administration results in reduced hyperkeratinization. 61. The method of any previous embodiment, such as embodiments 49-60, wherein the topical administration results in IGF1 signaling modulation. 62. The method of any previous embodiment, such as embodiments 49-61, wherein the topical administration results in mTORC1 signaling modulation. 63. The method of any previous embodiment, such as embodiments 49-62, wherein the topical administration results in SREBP1 modulation. 64. The method of any previous embodiment, such as embodiments 49-63, wherein the topical administration results in Foxp3 negative Treg cell accumulation. 65. The method of any previous embodiment, such as embodiments 49-64, wherein the topical administration results in decreased Th1 inflammation. 66. The method of any previous embodiment, such as embodiments 49-65, wherein the topical administration results in decreased Th17 inflammation. 67. The method of any previous embodiment, such as embodiments 47-66, wherein an acne status improvement comprises a GAGS percent change of over 30% in four weeks. 68. The method of any previous embodiment, such as embodiments 47-67, wherein an acne status improvement comprises a GAGS percent change of over 50% in eight weeks. 69. The method of any previous embodiment, such as embodiments 47-68, wherein an acne status improvement comprises a DLQI reduction of at least 30% in two weeks. 70. The method of any previous embodiment, such as embodiments 47.69, wherein an acne status improvement comprises a DLQI reduction of at least 70% in four weeks. 71. The method of any previous embodiment, such as embodiments 47-70, wherein the composition comprises a chemical any previous embodiment, such as embodiments 2 to 29. 72. A method of ameliorating a male pattern hair loss disorder, comprising administering a composition comprising an aqueous carrier, an alpha-hydroxy acid (AHA) at a concentration of from 0.1-20%, a nitric oxide (NO) precursor at a concentration of from 0.01-1%; monitoring acne status, and observing an acne status improvement. 73. The method of any previous embodiment, such as embodiment 72, wherein the administration comprises mixing a first constituent comprising an aqueous carrier and an alpha-hydroxy acid (AHA) at a concentration of from 0.1-20%, and a second constituent comprising an aqueous carrier and a nitric oxide (NO) precursor at a concentration of from 0.01-1%, 74. The method of any previous embodiment, such as embodiments 72-73, wherein the administration comprises aerosol administration. 75. The method of any previous embodiment, such as embodiment 74, wherein the topical administration results in intradermal delivery of NO to a target. 76. The method of any previous embodiment, such as embodiments 74-75, wherein the aerosol administration results in promotion of skin blood flow. 77. The method of any previous embodiment, such as embodiments 74-76, wherein the aerosol administration results in inhibition of steroidogenesis. 78. The method of any previous embodiment, such as embodiments 74-77, wherein the aerosol administration results in reduction of inflammation. 79. The method of any previous embodiment, such as embodiments 74-78, wherein the aerosol administration results in hair follicle formation. 80. The method of any previous embodiment, such as embodiments 74.79, wherein the aerosol administration results in increased hair follicle density. 81. The method of any previous embodiment, such as embodiments 74-80, wherein the aerosol administration results in hair follicle stem cell development. 82. The method of any previous embodiment, such as embodiments 74-81, wherein the aerosol administration results in hair shaft elongation. 83. The method of any previous embodiment, such as embodiments 74-82, wherein the aerosol administration results in a cumulative hair thickness increase of at least 10% in 12 weeks. 84. The method of any previous embodiment, such as embodiments 74.83, wherein the aerosol administration results in results in a cumulative hair thickness increase of at least 25% in 24 weeks. 85. The method of any previous embodiment, such as embodiments 74-84, wherein the aerosol administration results in an increase in the follicular units per unit area of at least 5% in 12 weeks. 86. The method of any previous embodiment, such as embodiments 74-85, wherein the aerosol administration results in an increase in the follicular units per unit area of at least 20% in 24 weeks. 87. A method of ameliorating an age related skin damage, comprising administering a composition comprising an aqueous carrier, an alpha-hydroxy acid (AHA) at a concentration of from 0.1-20%, a nitric oxide (NO) precursor at a concentration of from 0.01-1%; monitoring acne status, and observing an acne status improvement. 88. The method of any previous embodiment, such as embodiment 87, wherein the administration comprises mixing a first constituent comprising an aqueous carrier and an alpha-hydroxy acid (AHA) at a concentration of from 0.1-20%, and a second constituent comprising an aqueous carrier and a nitric oxide (NO) precursor at a concentration of from 0.01-1%, 89. The method of any previous embodiment, such as embodiment 87, wherein the administration comprises topical administration. 90. The method of any previous embodiment, such as embodiment 89, wherein the topical administration results in intradermal delivery of NO to a target. 91. The method of any previous embodiment, such as embodiment 89, wherein the topical administration results in promotion of skin blood flow. 92. The method of any previous embodiment, such as embodiments 89-91, wherein the topical administration results in inhibition of steroidogenesis. 93. The method of any previous embodiment, such as embodiments 89-92, wherein the topical administration results in reduction of inflammation. 94. A method of ameliorating a skin disorder, comprising delivering NO to an intradermal target through a topically administered medicament. 95. The method of any previous embodiment, such as embodiment 94, wherein the NO remains stable at the intradermal target. 96. A method of ameliorating a skin disorder, comprising identifying a patient having a skin disorder, identifying an intradermal target related to the skin disorder, delivering a therapeutic to the intradermal target, and monitoring amelioration of the skin disorder. 97. A method of modulating a signaling pathway, comprising identifying a disorder implicating the signaling pathway in an individual, delivering NO to an intradermal target constituent of the signaling pathway through a topically administered medicament, and monitoring activity of the signaling pathway. 96. 98. The method of any previous embodiment, such as embodiment 97, comprising monitoring the disorder.

Partial List of Definitions

As used herein, the term "about" when modifying a number a number refers to a range spanning that number plus or minus 10% of that number, while when modifying a range refers to an extended range spanning from 10% below the lower limit listed for the range to 10% above the higher limit listed for the range.

As used herein, an "aerosol" is a jet comprising fluid such as may be directed to a target area. The aerosol is in some cases individual droplets, while in other cases the aerosol comprises a merged stream or two separate streams of fluid such as the fluids of the compositions herein.

As used herein, the phrase "at least one selected from" a list of, for example A, B, and C, refers to a set comprising at least one member of the set, such as A, A and B, A and C, A B and C, B, B and C, or C, alone if described with 'consisting' of or in combination with other members if the set is described with 'comprising.'

As used herein, "intradermal space," "intradermal region," and similar terms refer to the cells or tissues beneath the epidermis and subcutaneous tissue. These terms are in some cases synonymous with "dermis" as presented in FIG. 1.

EXAMPLES

Example 1. A paired precursor composition and releasing composition are given below. The compositions are formulated with butylene glycol to form a paste which is readily massaged into the skin.

The precursor composition comprises water at >75%, butylene glycol at 5-10%, Succinoglycan at 0.1-1%, phenoxyethanol at 0.1-1%, Carbomer at 0.1-1%, sodium nitrate at 0.1-1%, ethylhexylglycerin at 0.1-1%, allantoin at 0.1-1%, parfum at <0.1%, Sodium sulfate at <0.1%, Sodium chlorate at trace levels, Geraniol at trace levels, linalool at trace levels, benzyl benzoate at trace levels, citronellol at trace levels, and hexyl cinnamal at trace levels. Sodium nitrite harbors the stably bound NO, which is not released at the pH of the precursor composition.

The releasing composition comprises water at >75%, butylene glycol at 5-10%, sodium polyacrylate at 1-5%, salicylic acid at 1-5%, citric acid at 1-5%, succinoglycan at 0.1-1%, glycerin at 0.1-1%, ascorbyl glucoside at 0.1-1%, sodium citrate at 0.1-1%, sodium hyaluronate at 0.1-1%, carbomer at 0.1-1%, sodium hydroxide at 0.1-1%, parfum at <0.1%, aloe barbadensis leaf juice at <0.1%, *Chamomilla recutita* flower extract at <0.1%, sodium sulfate at <0.1%, Sodium chlorate at trace levels, Geraniol at trace levels, linalool at trace levels, benzyl benzoate at trace levels, citronellol at trace levels, and hexyl cinnamal at trace levels. The releasing composition has a pH substantially lower than that of the precursor composition, such that upon their mixing, nitrite breaks down into NO and N2. Citric acid serves as a NO binding moiety, while ascorbyl glucoside prevents nitrite from undergoing detrimental cross-reactions.

The two compositions are combined in a 1:1 ratio to from an activation composition comprising water at >75%, butylene glycol at 5-10%, sodium polyacrylate at 0.5-2.5%, salicylic acid at 0.5-2.5%, citric acid at 0.5-2.5%, phenoxyethanol at >0.5%, Carbomer at >0.5%, sodium nitrate at >0.5%, ethylhexylglycerin at >0.5%, allantoin >0.5%, succinoglycan at 0.1-1%, glycerin at 0.1-1%, ascorbyl glucoside at 0.1-1%, sodium citrate at 0.1.1%, sodium hyaluronate at 0.1-1%, carbomer at 0.1-1%, sodium hydroxide at 0.1-19%, parfum at <0.1%, Sodium sulfate at <0.1%, Sodium chlorate at trace levels, Geraniol at trace levels, linalool at trace levels, benzyl benzoate at trace levels, citronellol at trace levels, and hexyl cinnamal at trace levels, aloe barbadensis leaf juice at <0.1%, *Chamomilla recutita* flower extract at <0.1%. This composition further comprises a steady state of NO-citric acid complexes.

Example 2. A paired precursor composition and releasing composition are given below. The compositions are formulated to form a thin liquid which is readily sprayed onto the scalp.

The precursor composition comprises water and 0.1-1% sodium nitrite.

The releasing composition comprises water, citric acid at 1-10%, hyaluronic acid at 1-10%, retinyl palmitate at 0.01-1%, tocopherol acetate at 0.01-1%, and sodium hydroxide at 0.01-1%.

The resulting activation composition comprises water, 0.05-0.5% sodium nitrate, the nitrite of which will break down into N2 and NO, citric acid at 0.5-5%, hyaluronic acid at 0.5-0.5%, retinyl palmitate at 0.005-0.5%, tocopherol at 0.005-0.5%, and sodium hydroxide at 0.005-0.5%. This composition further comprises a steady state of NO-citric acid complexes.

Example 3. A paired precursor composition and releasing composition are given below. The compositions are formulated with butylene glycol to form a paste which is readily massaged into the skin.

The precursor composition comprises water at >75%, butylene glycol at 5-10%, Succinoglycan at 0.1-1%, phenoxyethanol at 0.1-1%, Carbomer at 0.1-1%, sodium nitrate at 0.1-1%, ethylhexylglycerin at 0.1-1%, allantoin at 0.1-1%, parfum at <0.1%, Sodium nitrite harbors the stably bound NO, which is not released at the pH of the precursor composition.

The releasing composition comprises water at >75%, butylene glycol at 5-10%, citric acid at 1-5%, succinoglycan at 0.1-1%, ascorbyl glucoside at 0.1-1%, sodium citrate at 0.1-1%, sodium hyaluronate at 0.1-1%, carbomer at 0.1-1%, sodium hydroxide at 0.1-1%, and parfum at <0.1%. The releasing composition has a pH substantially lower than that of the precursor composition, such that upon their mixing, nitrite breaks down into NO and N2. Citric acid serves as a NO binding moiety, while ascorbyl glucoside prevents nitrite from undergoing detrimental cross-reactions.

The two compositions are combined in a 1:1 ratio to from an activation composition comprising water at >75%, butylene glycol at 5-10%, citric acid at 0.5-2.5%, phenoxyethanol at >0.5%, Carbomer at >0.5%, sodium nitrate at >0.5%, ethylhexylglycerin at >0.5%, allantoin >0.5%, succinoglycan at 0.1-1%, ascorbyl glucoside at 0.1-1%, sodium citrate at 0.1-1%, sodium hyaluronate at 0.1-1%, carbomer at 0.1-1%, sodium hydroxide at 0.1-1%, and parfum at <0.1%. This composition further comprises a steady state of NO-citric acid complexes.

Example 4. A paired precursor composition and releasing composition are given below. The compositions are formulated with butylene glycol to form a paste which is readily massaged into the skin.

The precursor composition comprises water at >75%, butylene glycol at 5-10%, Succinoglycan at 0.1-1%, phenoxyethanol at 0.1-1%, Carbomer at 0.1-1%, sodium nitrate at 0.1.1%, ethylhexylglycerin at 0.1.1%, allantoin at 0.1-1%, parfum at <0.1%, Sodium sulfate at <0.1%, Sodium chlorate at trace levels, Geraniol at trace levels, linalool at trace levels, benzyl benzoate at trace levels, citronellol at trace levels, and hexyl cinnamal at trace levels. Sodium nitrite harbors the stably bound NO, which is not released at the pH of the precursor composition.

The releasing composition comprises water at >75%, butylene glycol at 5-10%, sodium polyacrylate at 1-5%, salicylic acid at 1-5%, glycolic acid at 1-5%, succinoglycan at 0.1-1%, glycerin at 0.1-1%, ascorbyl glucoside at 0.1-1%, sodium citrate at 0.1-1%, sodium hyaluronate at 0.1-1%, carbomer at 0.1-1%, sodium hydroxide at 0.1-1%, parfum at <0.1%, aloe barbadensis leaf juice at <0.1%, *Chamomilla recutita* flower extract at <0.1%, sodium sulfate at <0.1%, Sodium chlorate at trace levels, Geraniol at trace levels, linalool at trace levels, benzyl benzoate at trace levels, citronellol at trace levels, and hexyl cinnamal at trace levels. The releasing composition has a pH substantially lower than that of the precursor composition, such that upon their mixing, nitrite breaks down into NO and N2. Glycolic acid serves as a NO binding moiety, while ascorbyl glucoside prevents nitrite from undergoing detrimental cross-reactions.

The two compositions are combined in a 1:1 ratio to from an activation composition comprising water at >75%, butylene glycol at 5-10%, sodium polyacrylate at 0.5.2.5%, salicylic acid at 0.5-2.5%, glycolic acid at 0.5-2.5%, phenoxyethanol at >0.5%, Carbomer at >0.5%, sodium nitrate at >0.5%, ethylhexylglycerin at >0.5%, allantoin >0.5%, succinoglycan at 0.1-1%, glycerin at 0.1-1%, ascorbyl glucoside at 0.1-1%, sodium citrate at 0.1-1%, sodium hyaluronate at 0.1-1%, carbomer at 0.1-1%, sodium hydroxide at 0.1-1%, parfum at <0.1%, Sodium sulfate at <0.1%, Sodium chlorate at trace levels, Geraniol at trace levels, linalool at trace levels, benzyl benzoate at trace levels, citronellol at trace levels, and hexyl cinnamal at trace levels, aloe barbadensis leaf juice at <0.1%, *Chamomilla recutita* flower extract at <0.1%. This composition further comprises a steady state of NO-glycolic acid complexes.

Example 5. A paired precursor composition and releasing composition are given below. The compositions are formulated to form a thin liquid which is readily sprayed onto the scalp.

The precursor composition comprises water and 0.1-1% sodium nitrite.

The releasing composition comprises water, glycolic acid at 1-10%, hyaluronic acid at 1-10%, retinyl palmitate at 0.01-1%, tocopherol acetate at 0.01-1%, and sodium hydroxide at 0.01-1%.

The resulting activation composition comprises water, 0.05-0.5% sodium nitrate, the nitrite of which will break down into N2 and NO, glycolic acid at 0.5-5%, hyaluronic acid at 0.5-5%, retinyl palmitate at 0.005-0.5%, tocopherol at 0.005-0.5%, and sodium hydroxide at 0.005-0.5%. This composition further comprises a steady state of NO-glycolic acid complexes.

Example 6. A paired precursor composition and releasing composition are given below. The compositions are formulated with butylene glycol to form a paste which is readily massaged into the skin.

The precursor composition comprises water at >75%, butylene glycol at 5-10%, Succinoglycan at 0.1-1%, phenoxyethanol at 0.1-1%, Carbomer at 0.1-1%, sodium nitrate at 0.1-1%, ethylhexylglycerin at 0.1-1%, allantoin at 0.1-1%, parfum at <0.1%, Sodium nitrite harbors the stably bound NO, which is not released at the pH of the precursor composition.

The releasing composition comprises water at >75%, butylene glycol at 5-10%, glycolic acid at 1-5%, succinoglycan at 0.1-1%, ascorbyl glucoside at 0.1-1%, sodium citrate at 0.1-1%, sodium hyaluronate at 0.1-1%, carbomer at 0.1-1%, sodium hydroxide at 0.1-1%, and parfum at <0.1%. The releasing composition has a pH substantially lower than that of the precursor composition, such that upon their mixing, nitrite breaks down into NO and N2. Glycolic acid serves as a NO binding moiety, while ascorbyl glucoside prevents nitrite from undergoing detrimental cross-reactions.

The two compositions are combined in a 1:1 ratio to from an activation composition comprising water at >75%, butylene glycol at 5-10%, glycolic acid at 0.5-2.5%, phenoxyethanol at >0.5%, Carbomer at >0.5%, sodium nitrate at >0.5%, ethylhexylglycerin at >0.5%, allantoin >0.5%, succinoglycan at 0.1-1%, ascorbyl glucoside at 0.1-1%, sodium citrate at 0.1-1%, sodium hyaluronate at 0.1-1%, carbomer at 0.1-1%, sodium hydroxide at 0.1.1%, and parfum at <0.1%. This composition further comprises a steady state of NO-glycolic acid complexes.

Example 7. A paired precursor composition and releasing composition are given below. The compositions are formulated with butylene glycol to form a paste which is readily massaged into the skin.

The precursor composition comprises water at >75%, butylene glycol at 5-10%, Succinoglycan at 0.1-1%, phenoxyethanol at 0.1-1%, Carbomer at 0.1-1%, sodium nitrate at 0.1-1%, ethylhexylglycerin at 0.1-1%, allantoin at 0.1-1%, parfum at <0.1%, Sodium sulfate at <0.1%, Sodium chlorate at trace levels, Geraniol at trace levels, linalool at trace levels, benzyl benzoate at trace levels, citronellol at trace levels, and hexyl cinnamal at trace levels. Sodium nitrite harbors the stably bound NO, which is not released at the pH of the precursor composition.

The releasing composition comprises water at >75%, butylene glycol at 5-10%, sodium polyacrylate at 1-5%, salicylic acid at 1-5%, hydroxycapric acid at 1-5%, succinoglycan at 0.1-1%, glycerin at 0.1-1%, ascorbyl glucoside at 0.1-1%, sodium citrate at 0.1-1%, sodium hyaluronate at 0.1-1%, carbomer at 0.1-1%, sodium hydroxide at 0.1-1%, parfum at <0.1%, aloe barbadensis leaf juice at <0.1%, *Chamomilla recutita* flower extract at <0.1%, sodium sulfate at <0.1%, Sodium chlorate at trace levels, Geraniol at trace levels, linalool at trace levels, benzyl benzoate at trace levels, citronellol at trace levels, and hexyl cinnamal at trace levels. The releasing composition has a pH substantially lower than that of the precursor composition, such that upon their mixing, nitrite breaks down into NO and N2. Hydroxycapric acid serves as a NO binding moiety, while ascorbyl glucoside prevents nitrite from undergoing detrimental cross-reactions.

The two compositions are combined in a 1:1 ratio to from an activation composition comprising water at >75%, butylene glycol at 5-10%, sodium polyacrylate at 0.5-2.5%, salicylic acid at 0.5-2.5%, hydroxycapric acid at 0.5-2.5%, phenoxyethanol at >0.5%, Carbomer at >0.5%, sodium nitrate at >0.5%, ethylhexylglycerin at >0.5%, allantoin >0.5%, succinoglycan at 0.1-1%, glycerin at 0.1-1%, ascorbyl glucoside at 0.1-1%, sodium citrate at 0.1-1%, sodium hyaluronate at 0.1-1%, carbomer at 0.1-1%, sodium hydroxide at 0.1-1%, parfum at <0.1%, Sodium sulfate at <0.1%, Sodium chlorate at trace levels, Geraniol at trace levels, linalool at trace levels, benzyl benzoate at trace levels, citronellol at trace levels, and hexyl cinnamal at trace levels, aloe barbadensis leaf juice at <0.1%, *Chamomilla recutita* flower extract at <0.1%. This composition further comprises a steady state of NO-hydroxycapric acid complexes.

Example 8. A paired precursor composition and releasing composition are given below. The compositions are formulated to form a thin liquid which is readily sprayed onto the scalp.

The precursor composition comprises water and 0.1-1% sodium nitrite.

The releasing composition comprises water, hydroxycapric acid at 1-10%, hyaluronic acid at 1-10%, retinyl palmitate at 0.01-1%, tocopherol acetate at 0.01-1%, and sodium hydroxide at 0.01-1%.

The resulting activation composition comprises water, 0.05-0.5% sodium nitrate, the nitrite of which will break down into N2 and NO, hydroxycapric acid at 0.5-5%, hyaluronic acid at 0.5-5%, retinyl palmitate at 0.005-0.5%, tocopherol at 0.005-0.5%, and sodium hydroxide at 0.005-0.5%. This composition further comprises a steady state of NO-hydroxycapric acid complexes.

Example 9. A paired precursor composition and releasing composition are given below. The compositions are formulated with butylene glycol to form a paste which is readily massaged into the skin.

The precursor composition comprises water at >75%, butylene glycol at 5-10%, Succinoglycan at 0.1-1%, phenoxyethanol at 0.1-1%, Carbomer at 0.1-1%, sodium nitrate at 0.1-1%, ethylhexylglycerin at 0.1-1%, allantoin at 0.1-1%, parfum at <0.1%, Sodium nitrite harbors the stably bound NO, which is not released at the pH of the precursor composition.

The releasing composition comprises water at >75%, butylene glycol at 5-10%, hydroxycapric acid at 1-5%, succinoglycan at 0.1-1%, ascorbyl glucoside at 0.1-1%, sodium citrate at 0.1-1%, sodium hyaluronate at 0.1-1%, carbomer at 0.1-1%, sodium hydroxide at 0.1-1%, and parfum at <0.1%. The releasing composition has a pH substantially lower than that of the precursor composition, such that upon their mixing, nitrite breaks down into NO and N2. Hydroxycapric acid serves as a NO binding moiety, while ascorbyl glucoside prevents nitrite from undergoing detrimental cross-reactions.

The two compositions are combined in a 1:1 ratio to from an activation composition comprising water at >75%, butylene glycol at 5-10%, hydroxycapric acid at 0.5-2.5%, phenoxyethanol at >0.5%, Carbomer at >0.5%, sodium nitrate at >0.5%, ethylhexylglycerin at >0.5%, allantoin >0.5%, succinoglycan at 0.1-1%, ascorbyl glucoside at 0.1-1%, sodium citrate at 0.1-1%, sodium hyaluronate at 0.1-1%, carbomer at 0.1-1%, sodium hydroxide at 0.1-1%, and parfum at <0.1%. This composition further comprises a steady state of NO-hydroxycapric acid complexes.

Example 10. A scalp health composition consistent with Examples 2, 5 or 8 was used to treat a cohort of individuals exhibiting male pattern baldness. Precursor and releasing compositions were concurrently applied in a single spray flow to individual's exposed skin. Precursor and releasing compositions mixed concurrently with ejection of the spray from the administration system.

Administration was performed twice daily for at least 24 weeks. At 12 weeks and 24 weeks, participants were assessed as to their number of hair follicles per unit area, follicle stem cell health, hair shaft elongation and hair growth rate.

Cumulative hair thickness (mm/cm2) was found to improve by over 10% at 12 weeks and by over 25% at 24 weeks. The number of follicular units (N/cm2) was observed to increase by about 7% by 12 weeks and by over 20% at week 24. These results compare favorably to results observed upon use of market leading hair restoration products, use of which leads to an increase of follicular units (N/cm2) by 13% at 24 weeks. The data are presented in FIG. 4 and FIG. 5.

Example 11. A precursor composition consistent with a broad range of releasing compositions is presented below. The precursor composition comprises water at >75%, glycolic acid at 1-10%, hyaluronic acid at 1-10%, ascorbic acid at 0.01-1%, sodium nitrite at 0.01-1%, and sodium hydroxide at 0.01-1%. Sodium nitrite harbors the stably bound NO, which is not released at the pH of the precursor composition.

I claim:

1. A composition comprising an aqueous carrier, an alpha-hydroxy acid (AHA) at a concentration of from 0.1-20%, a nitric oxide (NO) precursor at a concentration of from 0.01-1%, and a succinoglycan.

2. The composition of claim 1, wherein the AHA is glycolic acid.

3. The composition of claim 1, wherein the AHA is present at a concentration of 1%-5%.

4. The composition of claim 1, wherein the NO precursor is Sodium nitrite.

5. The composition of claim 1, wherein the NO precursor is present at a concentration of 0.001-0.5%.

6. The composition of claim 1, comprising glycol.

7. The composition of claim 6, wherein the glycol is present at a concentration of 1-20%.

8. The composition of claim 7, wherein the glycol is present at a concentration of 2.5-5%.

9. The composition of claim 1, comprising hyaluronic acid.

10. The composition of claim 1, comprising retinyl palmitate.

11. The composition of claim 1, comprising tocopherol acetate.

12. The composition of claim 1, comprising Sodium hydroxide.

13. The composition of claim 1, comprising polyacrylate.

14. The composition of claim 1, comprising Salicylic acid.

15. The composition of claim 1, comprising ascorbic acid.

16. The composition of claim 1, comprising ascorbyl glucoside.

17. The composition of claim 1, comprising Sodium citrate.

18. The composition of claim 1, comprising carbomer.

19. The composition of claim 1, comprising sodium chloride.

20. The composition of claim 1, comprising sodium sulfate.

21. The composition of claim 1, comprising geraniol.

22. The composition of claim 1, comprising linalool.

23. The composition of claim 1, comprising benzyl benzoate.

24. The composition of claim 1, comprising citronellol.

25. The composition of claim 1, comprising hexyl cinnamal.

26. The composition of claim 1, comprising phenoxyethanol.

27. The composition of claim 1, comprising ethylhexylglycerin.

28. The composition of claim 1, comprising allantoin.

29. The composition of claim 1, wherein the composition is vegan.

30. The composition of claim 1, wherein the composition is hypoallergenic.

* * * * *